(12) United States Patent
Xu et al.

(10) Patent No.: US 11,941,802 B2
(45) Date of Patent: Mar. 26, 2024

(54) DATA PROCESSING METHOD, MEANS AND SYSTEM

(71) Applicant: Alibaba Group Holding Limited, George Town (KY)

(72) Inventors: Minfeng Xu, Beijing (CN); Zhe Tang, Beijing (CN); Shuangrui Liu, Beijing (CN); Wenchao Guo, Beijing (CN); Jianqiang Ma, Beijing (CN)

(73) Assignee: Alibaba Group Holding Limited (KY)

( * ) Notice: Subject to any disclaimer, the term of this patent is extended or adjusted under 35 U.S.C. 154(b) by 184 days.

(21) Appl. No.: 17/210,256

(22) Filed: Mar. 23, 2021

(65) Prior Publication Data

US 2021/0303928 A1 Sep. 30, 2021

(30) Foreign Application Priority Data

Mar. 31, 2020 (CN) .......................... 202010244916.7

(51) Int. Cl.
*G06T 7/00* (2017.01)
*A61B 5/00* (2006.01)
(Continued)

(52) U.S. Cl.
CPC ............ *G06T 7/0012* (2013.01); *A61B 5/004* (2013.01); *A61B 5/7267* (2013.01);
(Continued)

(58) Field of Classification Search
CPC ......... G06T 7/0012; G06T 2207/10081; G06T 2207/20081; G06T 2207/30096;
(Continued)

(56) References Cited

U.S. PATENT DOCUMENTS

| 5,769,074 A | 6/1998 | Barnhill |
| 8,296,247 B2 | 10/2012 | Zhang |

(Continued)

FOREIGN PATENT DOCUMENTS

| CN | 108335282 | 7/2018 |
| CN | 110852285 | 2/2020 |

(Continued)

OTHER PUBLICATIONS

Lee et al. "Classification of femur fracture in pelvic X-ray images using meta-learned deep neural network", Sci Rep 10, 13694, Aug. 13, 2020. Retrieved on Jun. 3, 2021. Retrieved from <URL: https://www.nature.com/articles/s41598-020-70660-4> entire document.

*Primary Examiner* — Tom Y Lu
(74) *Attorney, Agent, or Firm* — Van Pelt, Yi & James LLP

(57) ABSTRACT

The present application discloses a method, device, and system for processing a medical image. The method includes obtaining, by one or more processors, a target image, segmenting, by the one or more processors, a target region image from the target image, wherein the target region image comprises a target object region in the target image, analyzing, by the one or more processors, the target region image based at least in part on a machine learning model, and obtaining by the one or more processors, a recognition result based at least in part on the analysis of the target region image.

20 Claims, 8 Drawing Sheets

(51) Int. Cl.
  *G06F 18/214* (2023.01)
  *G06F 18/2415* (2023.01)
  *G06F 18/40* (2023.01)
  *G06T 7/11* (2017.01)
  *G06V 10/778* (2022.01)

(52) U.S. Cl.
  CPC .......... *A61B 5/7275* (2013.01); *A61B 5/7475* (2013.01); *G06F 18/2148* (2023.01); *G06F 18/2415* (2023.01); *G06F 18/41* (2023.01); *G06T 7/11* (2017.01); *G06V 10/7788* (2022.01); *G06T 2207/10081* (2013.01); *G06T 2207/20081* (2013.01); *G06T 2207/30096* (2013.01); *G06V 2201/031* (2022.01)

(58) Field of Classification Search
  CPC . G06T 2207/20084; G06T 2207/30061; A61B 5/004; A61B 5/7275; A61B 5/7475; A61B 5/7485; G06F 18/2148; G06F 18/2415; G06F 18/04; G06F 18/241; G06V 10/7788; G06V 2201/031
  See application file for complete search history.

(56) References Cited

U.S. PATENT DOCUMENTS

| | | | |
|---|---|---|---|
| 8,543,519 B2 | 9/2013 | Guyon | |
| 9,589,374 B1 * | 3/2017 | Gao | ............ A61B 6/5211 |
| 9,980,704 B2 | 5/2018 | Gratacós Solsona | |
| 10,013,757 B2 | 7/2018 | Kim | |
| 10,127,659 B2 | 11/2018 | Hsieh | |
| 10,140,544 B1 * | 11/2018 | Zhao | ............ G06N 20/00 |
| 10,304,193 B1 * | 5/2019 | Wang | ............ G16H 50/20 |
| 10,354,171 B2 | 7/2019 | Hsieh | |
| 10,445,462 B2 | 10/2019 | Sorenson | |
| 10,452,813 B2 | 10/2019 | Sorenson | |
| 10,643,331 B2 | 5/2020 | Ghesu | |
| 10,740,901 B2 * | 8/2020 | Myronenko | ......... G06F 18/211 |
| 10,825,168 B2 | 11/2020 | Tegzes | |
| 2014/0088415 A1 | 3/2014 | Hielscher | |
| 2016/0300351 A1 | 10/2016 | Gazit | |
| 2016/0350919 A1 | 12/2016 | Steigauf | |
| 2017/0217102 A1 | 8/2017 | Mansi | |
| 2017/0337682 A1 | 11/2017 | Liao | |
| 2018/0028079 A1 | 2/2018 | Gurevich | |
| 2018/0253843 A1 | 9/2018 | Gillies | |
| 2018/0330207 A1 | 11/2018 | Zhou | |
| 2019/0110753 A1 | 4/2019 | Zhang | |
| 2019/0325621 A1 | 10/2019 | Wang | |
| 2020/0058126 A1 | 2/2020 | Wang | |
| 2020/0082534 A1 | 3/2020 | Nikolov | |
| 2020/0258227 A1 | 8/2020 | Liao | |
| 2021/0090738 A1 | 3/2021 | Bates | |
| 2022/0148282 A1 | 5/2022 | Takahashi | |
| 2023/0218169 A1 | 7/2023 | Yang | |

FOREIGN PATENT DOCUMENTS

| | | |
|---|---|---|
| JP | 2018175227 | 11/2018 |
| KR | 20140028534 | 3/2014 |
| WO | 2020026223 | 2/2020 |
| WO | 2020044840 | 3/2020 |

* cited by examiner

300

500

DATA PROCESSING METHOD, MEANS AND SYSTEM

CROSS REFERENCE TO OTHER APPLICATIONS

This application claims priority to People's Republic of China Patent Application No. 202010244916.7 entitled DATA PROCESSING METHOD, MEANS AND SYSTEM filed Mar. 31, 2020 which is incorporated herein by reference for all purposes.

FIELD OF THE INVENTION

The present application relates to a field of image processing technology. In particular, the present application relates to a data processing method, means, and system.

BACKGROUND OF THE INVENTION

In recent years, as computer technology has developed rapidly, image processing technology, which is intimately connected with computer technology, has become an indispensable method in modern medical treatment and diagnosis. As society continues to age, the need for image processing services continually grows. For example, if the images are medical images, a radiologist will need to review and consider thousands of images, and possibly tens of thousands of images every day. However, radiologists currently read each image one at a time, and the time spent reading each image is relatively long. Therefore, image reading involves heavy workloads and relatively low efficiency.

No effective solution has yet been put forward to address the problem described above.

BRIEF DESCRIPTION OF THE DRAWINGS

Various embodiments of the invention are disclosed in the following detailed description and the accompanying drawings.

The drawings described here are intended to further the understanding of the present invention and form a part of the present application. The illustrative embodiments of the present invention and the descriptions thereof are intended to explain the present invention and do not constitute inappropriate limitation of the present invention. Among the drawings.

DETAILED DESCRIPTION

Figure 1:
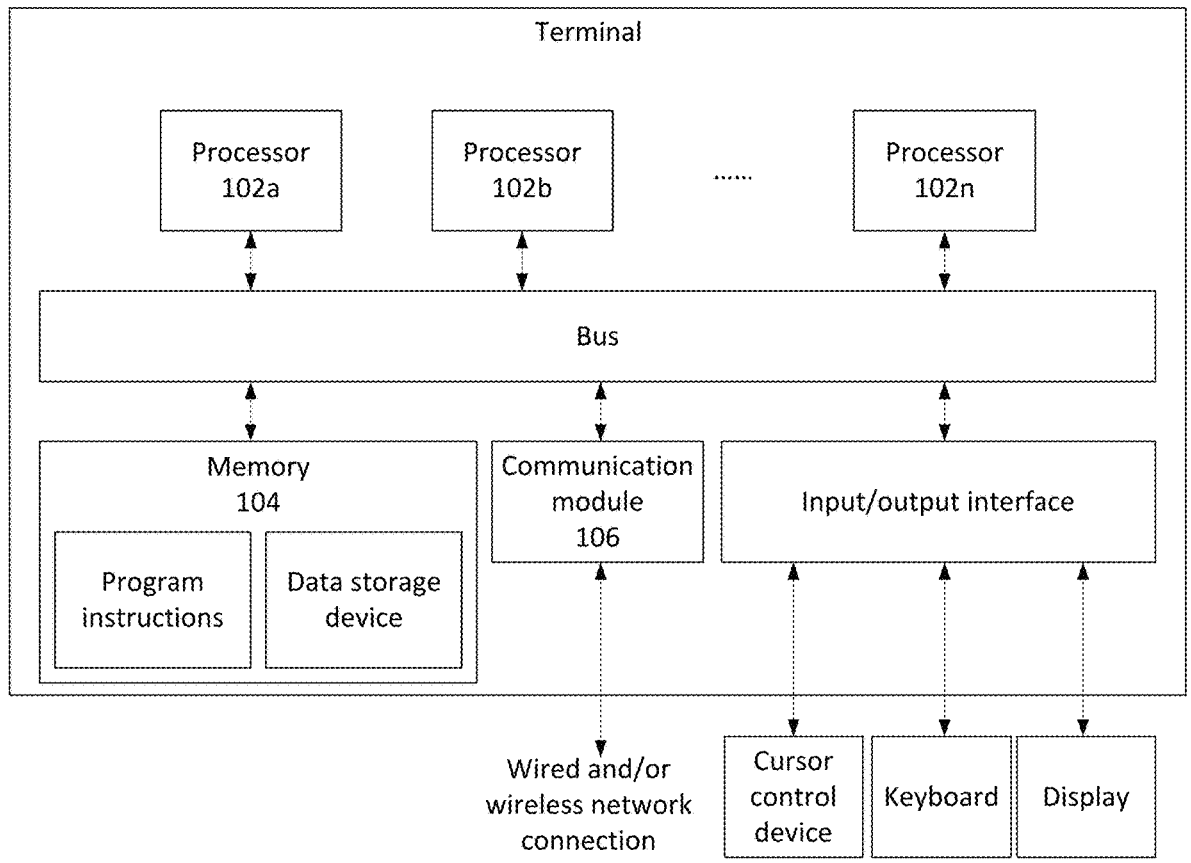
FIG. 1 is a hardware structural block diagram of a terminal according to various embodiments of the present application.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

In order to give persons skilled in the art a better understanding of the present invention, technical schemes in embodiments of the present invention are described clearly and completely in light of the drawings of the embodiments of the present invention. Obviously, the embodiments described are merely some of the embodiments of the present invention and are not all the embodiments. So long as no additional creative effort is expended, all other embodiments that are obtained by persons with ordinary skill in the art on the basis of embodiments in the present invention shall fall within the scope of protection of the present invention.

Please understand that the terms "first," "second," etc. in the description, claims, and drawings of the present invention are used to differentiate similar objects and are not necessarily used to describe their particular sequence or order. It should be understood that data used in this way may be switched as appropriate. Thus, embodiments of the present invention described herein can be implemented in sequences other than those shown or described herein. In addition, the terms "comprise" and "have" and the variations thereof are meant to be non-exclusive. For example, a process, method, system, product, or device containing a series of steps or units need not be limited to those steps or units that are clearly listed, but may comprise other steps or units that are not clearly listed or that are intrinsic to these processes, methods, products, or devices.

As used herein, a "terminal" generally refers to a device comprising one or more processors. A terminal can be a device used (e.g., by a user) within a network system and used to communicate with one or more servers. According to various embodiments of the present disclosure, a terminal includes components that support communication functionality. For example, a terminal can be a smart phone, a server, a machine of shared power banks, information centers (such as one or more services providing information such as traffic or weather, etc.), a tablet device, a mobile phone, a video phone, an e-book reader, a desktop computer, a laptop computer, a netbook computer, a personal computer, a Personal Digital Assistant (PDA), a Portable Multimedia Player (PMP), a mobile medical device, a camera, a wearable device (e.g., a Head-Mounted Device (HMD), electronic clothes, electronic braces, an electronic necklace, an electronic accessory, an electronic tattoo, or a smart watch), a kiosk such as a vending machine, a smart home appliance, vehicle-mounted mobile stations, or the like. A terminal can run various operating systems.

As used herein, a client refers to a terminal that communicates with a server. The client may be implemented on a terminal via one or more applications running on the terminal. For example, the client may refer to a mobile terminal that communicates with the server via one or more networks. The mobile terminal can run an application (e.g., a client application) that communicates with the server in connection with performing one or more operations at the mobile terminal. The client can communicate information to the server. In some embodiments, the information communicated from the client to the server includes one or more requests, etc. The client may also receive information from the server (e.g., via communication one or more networks). In some embodiments, the information that the client receives from the server includes information pertaining to an image analysis performed with respect to an image such as a medical image. For example, the information pertaining to an image analysis includes a classification of the image and/or an identification of target data that is determined based at least in part on the image (e.g., the medical image).

As used herein, a medical image may refer to an image comprising a representation of an organ (e.g., an organ of a living being). A medical image may be captured using a medical imaging technology. As an example, the medical imaging technology may be, but is not limited to, X-rays, gamma rays, nuclear magnetic resonance, or ultrasound. Various medical imaging technologies may be used for capturing medical images corresponding to different target organs. As an example, the organ for which a representation is provided in the medical image may include an organ in the body of a patient (e.g., a human, an animal, a living being, etc.). Examples of an organ include a brain, a heart, a lung, etc.

As used herein, reinforcement learning refers to a type of learning capable of taking environment-based actions to obtain expected benefits.

As used herein, an encoder-decoder model refers to a model framework in deep learning. The encoder-decoder model can be divided into two parts: an encoder network and a decoder network.

As used herein, UNet refers to a convolutional neural network. The UNet can be divided into two parts: a first half that is used in connection with feature extraction; and a second half that is used in connection with upsampling.

As used herein, a pyramid scene parsing network (PSP-Net) refers to a network that aggregates context information based on different regions to exploit global context information capabilities.

As used herein, DeepLabV3+(DeepLab) refers to a method of combining deep convolutional neural networks (DCNNs) and probabilistic graphical models (DenseCRFs). DeepLab puts forward an atrous spatial pyramid pooling module. The atrous spatial pyramid pooling module is used in connection with exploring multi-scale convolutional features and encoding global backgrounds based on image layers to obtain features.

As used herein, resnext refers to a homogeneous neural network. Resnext comprises multiple branches using the same topological structure. The number of channels of the feature map generated by each branch is n.

As used herein, Atrous Spatial Pyramid Pooling (ASPP) structure refers to a module that uses multi-scale information to further reinforce segmentation results.

As used herein, rigid transformation refers to a transformation of an object in which only a position (translation transformation) and direction (rotation transformation) of the object is changed, but the shape does not change.

As used herein, affine transformation refers to a transformation involving any inclination of a graphic and any expansion or contraction of a graphic in two directions.

As used herein, a model may refer to a defined process such as a process for analyzing an image. The model may include one or more conditions or instructions for performing the process.

According to various embodiments, a method for data processing is provided. The method for data processing may include performing an analysis on an image such as a medical image. A medical image may processed in connection with providing information that classifies the medical image and/or identifies an abnormality in the medical image (e.g., on the captured target organ), or other disease. The medical image may be processed to obtain target data such as information pertaining to a particular region of the medical image. In some embodiments, the processing of the medical image includes extracting one or more lesion regions and/or organ regions (e.g., human organ regions). The extraction of the one or more lesion regions and/or organ regions may be based at least in part on a segmentation of the medical image and quantitative analysis of the medical image or a segmented part of the medical image. Please note that the steps depicted in the flowcharts in the drawings can be executed in a computer system, such as a group of computers capable of executing commands. Moreover, although logical sequences are depicted in the flowcharts, the steps that are depicted or described may, in some situations, be executed in sequences other than those here.

FIG. 1 is a hardware structural block diagram of a terminal according to various embodiments of the present application.

Figure 2:
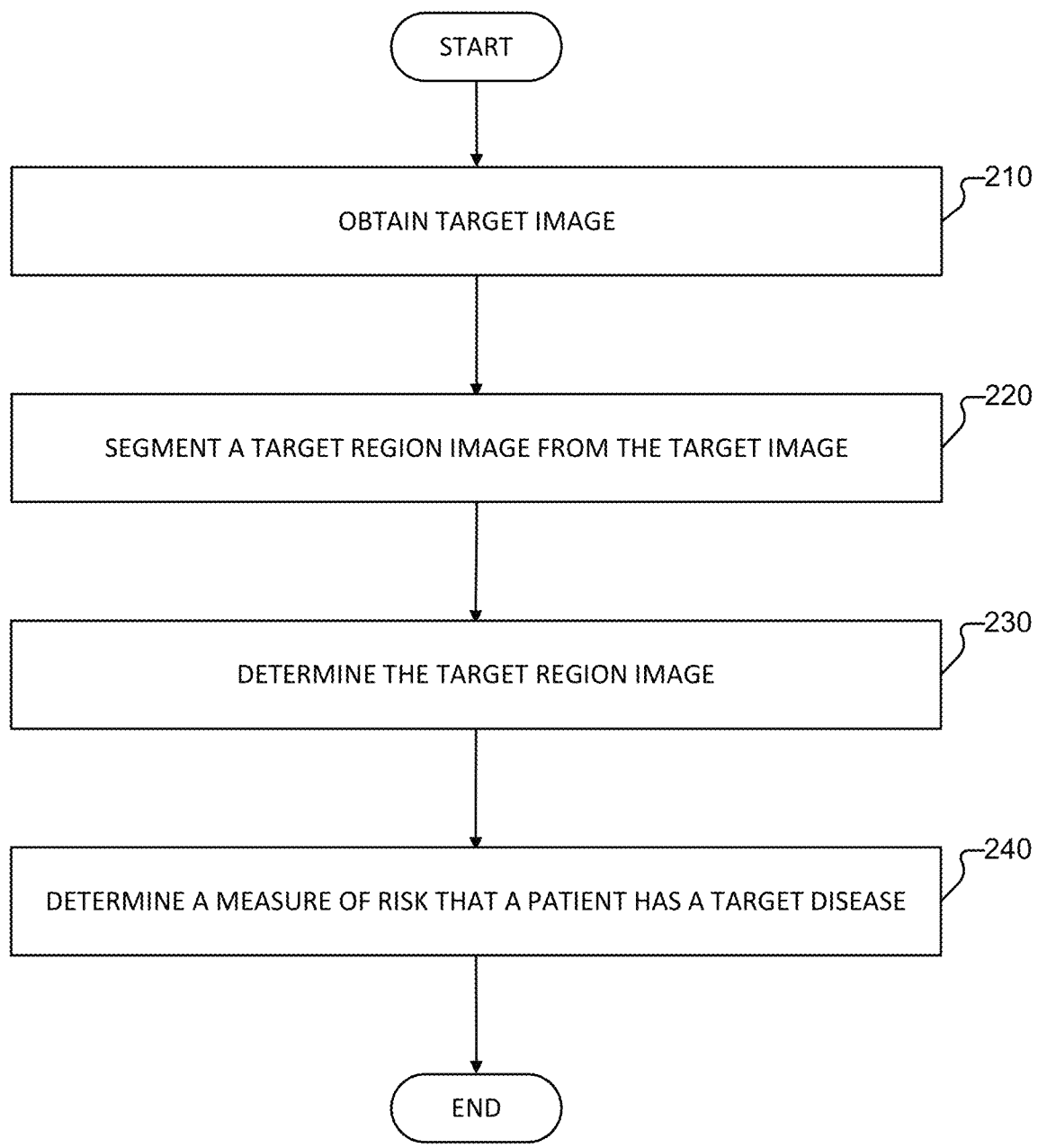
FIG. 2 is a flowchart of a method for data processing according to various embodiments of the present application.
Figure 4:
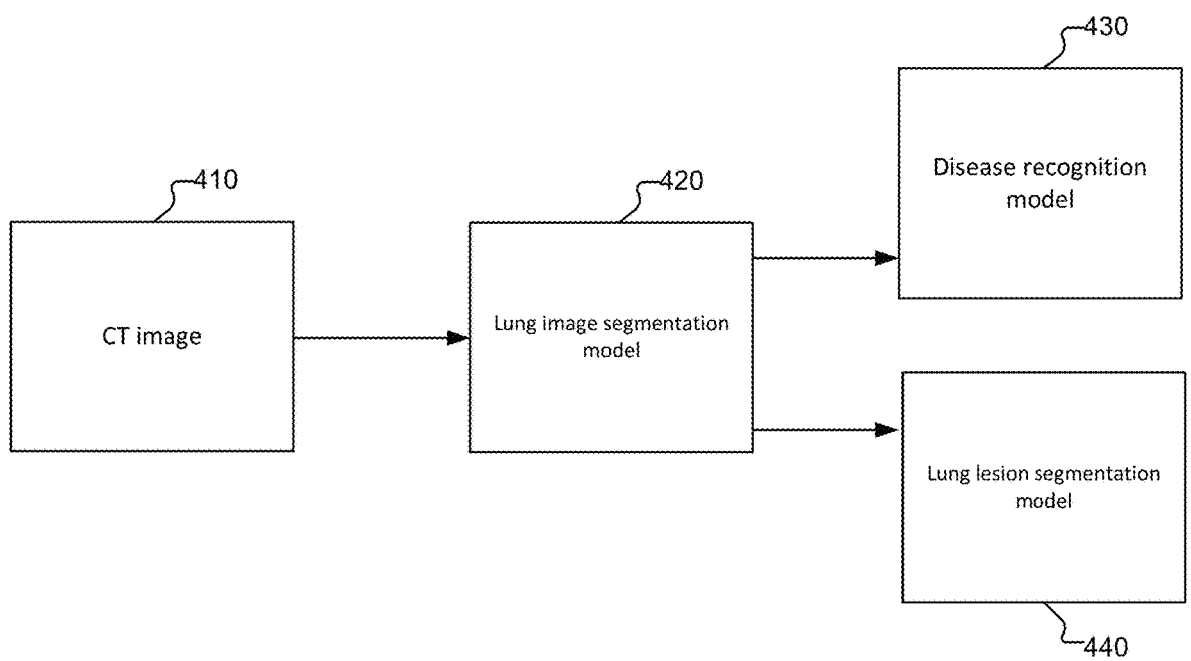
FIG. 4 is a block diagram of a method for data processing according to various embodiments of the present application.
Figure 5:
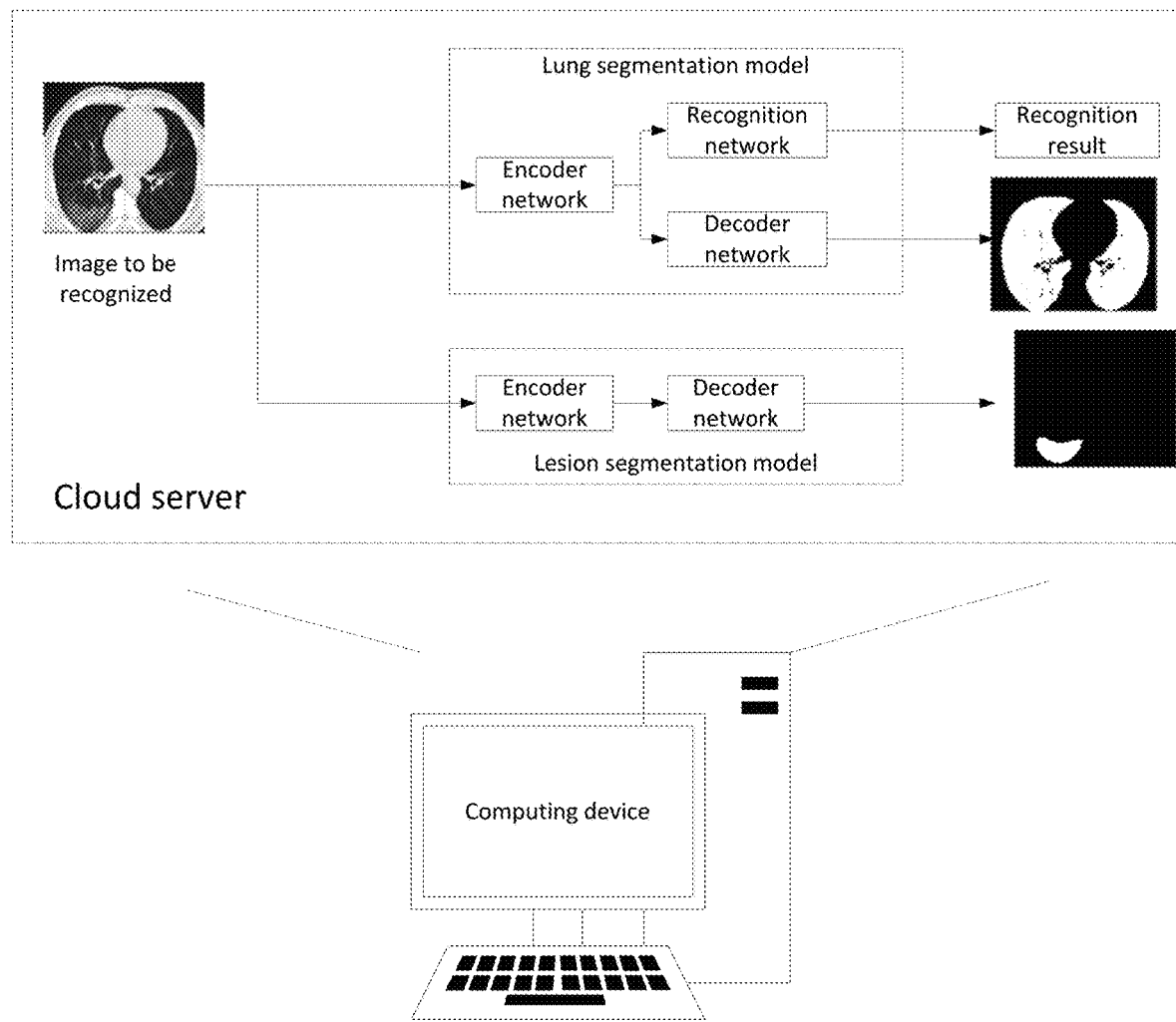
FIG. 5 is a diagram of a method for data processing according to various embodiments of the present application.
Figure 6:
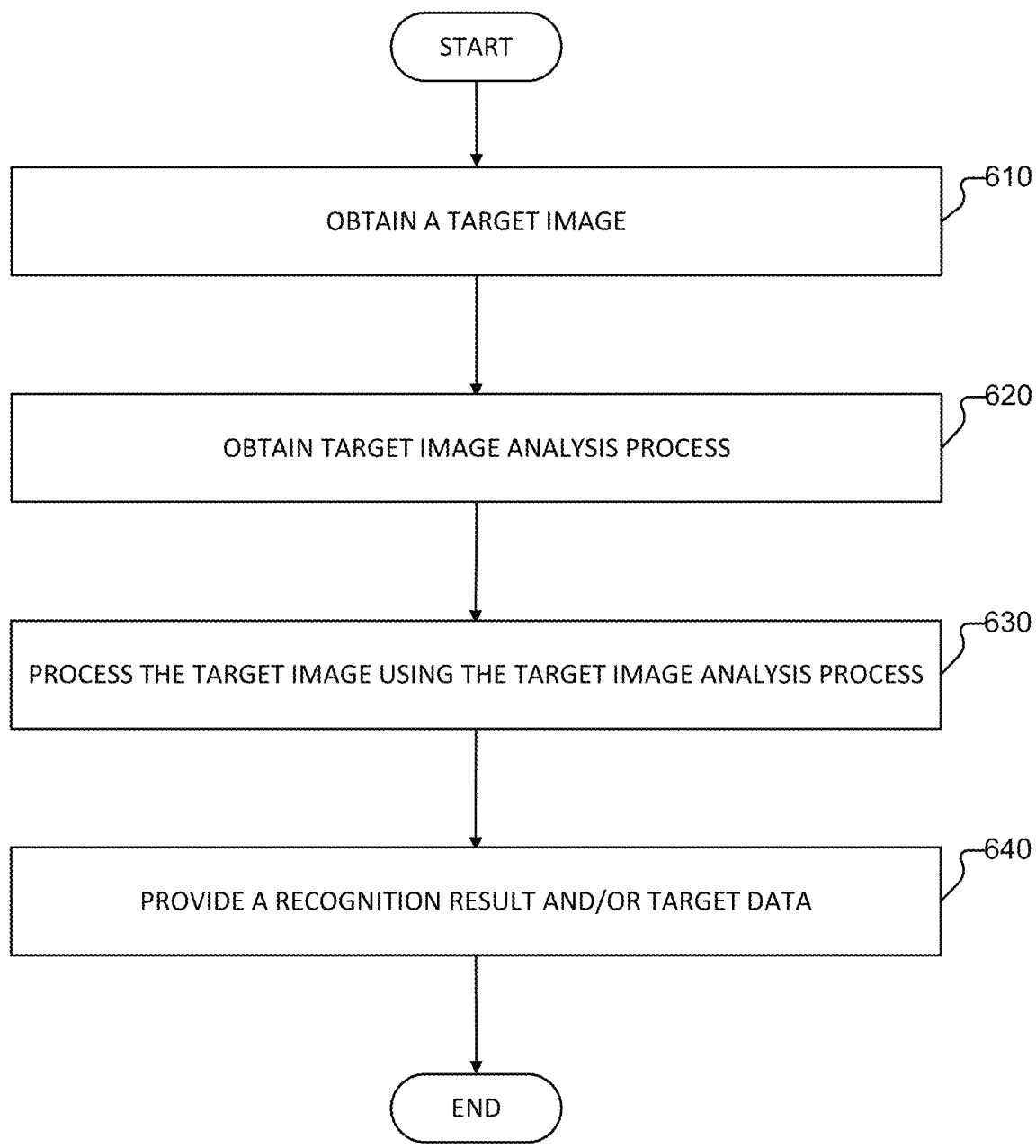
FIG. 6 is a flowchart of a method for data processing according to various embodiments of the present application.
Figure 7:
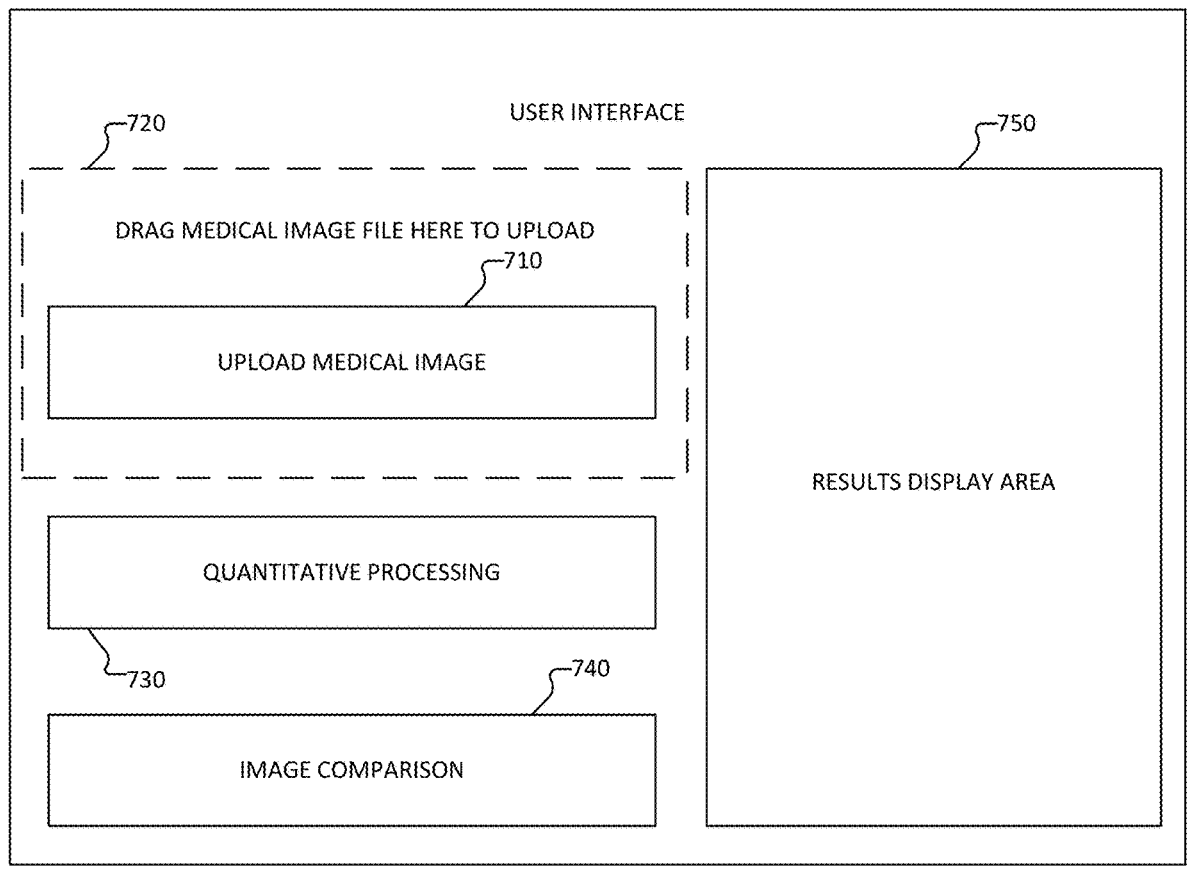
FIG. 7 is a diagram of an interface used in connection with processing an image according to various embodiments of the present application.
Figure 8:
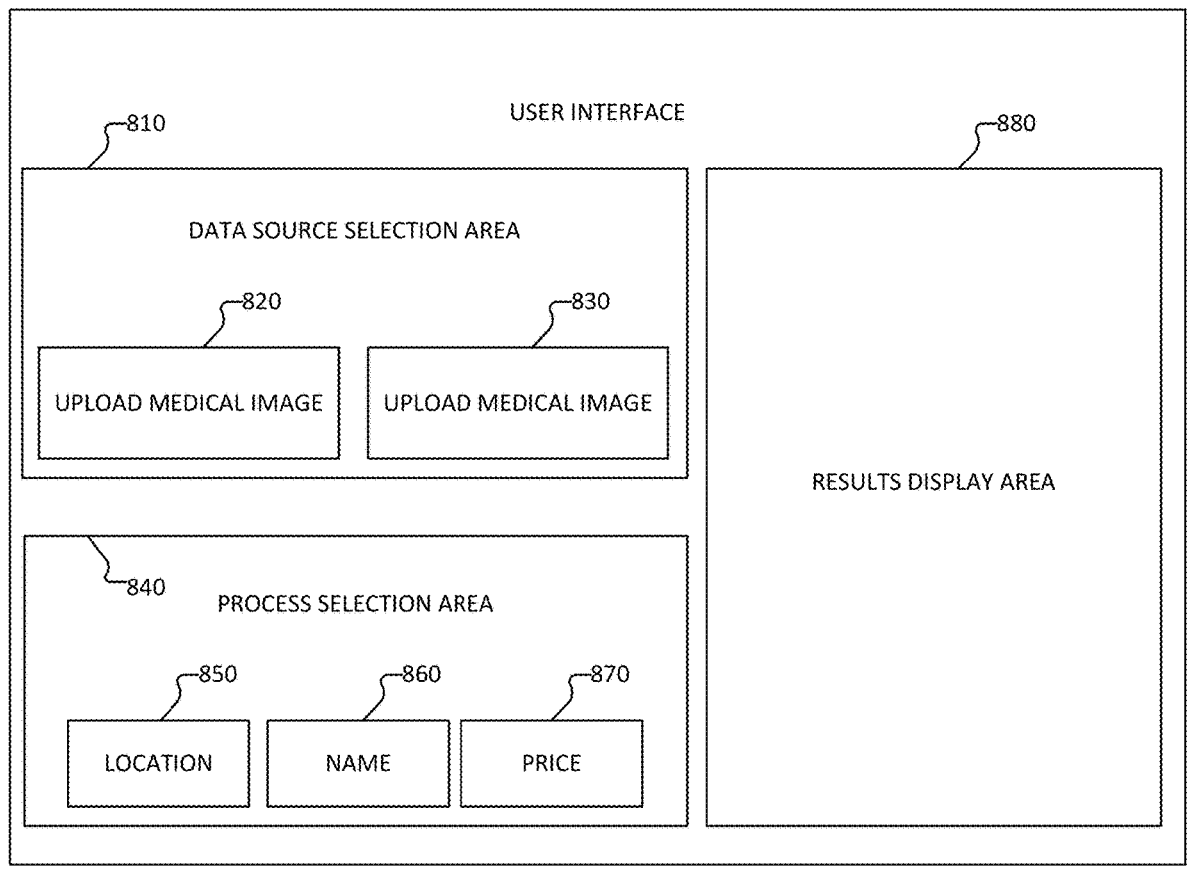
FIG. 8 is a diagram of an interface used in connection with processing an image according to various embodiments of the present application.

According to various embodiments, terminal 100 implements at least part of process 200 of FIG. 2, process 400 of FIG. 4, process 500 of FIG. 5, process 600 of FIG. 6, interface 700 of FIG. 7, and/or interface 800 of FIG. 8.

As shown in FIG. 1, terminal 100 may comprise one or more processors 102 (indicated by 102$a$, 102$b$, ..., 102$n$ in the drawing). Processors 102 may include, but are not limited to, processing means such as microprocessors (MCU) or programmable logic devices (FPGA). Terminal 100 may include memory 104 for storing data (e.g., information, executable instructions, medical information, data pertaining to a quantitative analysis of the medical information, etc.), and a communication module 106 for communication functions. Terminal 100 may include a display device, input/output interfaces (I/O interfaces), a universal serial bus (USB) port (may be included as a port among bus ports), a network interface, a power supply, and/or a camera. The terminal 100 of FIG. 1 is illustrative and does not impose restrictions on the structures of the electronic devices described above. For example, terminal 100 may further comprise more or fewer components than are shown in FIG. 1 or have a configuration different from the one shown in FIG. 1.

Please note that the one or more processors 102 and/or other data processing circuits may generally be referred to as "data processing circuits" in this document. All or part of the data processing circuits may be embodied as software, hardware, firmware, or any combination thereof. In addition, a data processing circuit can be a single, independent processing module or any of the other components that are fully or partially integrated with the terminal 100. The data processing circuits of various embodiments of the present application are used as a kind of processor control (e.g., selection of variable resistance terminal paths for connecting to interfaces).

Memory 104 may be used to store software programs and modules of the application software (e.g., program instructions/data storage means corresponding to a method for data processing, including a method for processing a medical image according to various embodiments of the present application). In connection with running software programs and modules stored in memory 104, processor 102 executes various function applications and data processing, (e.g., the processor implements the method for processing a medical image according to various embodiments of the present application). Memory 104 may comprise high-speed random access memory. Memory 104 comprises non-volatile memory, such as one or more magnetic storage devices, flash memory, or other non-volatile solid-state memory. In some embodiments, memory 104 comprises a memory that is remotely disposed relative to processor 102. Such remote memory may be connected to the terminal 100 via one or more networks. Examples of the network described above include, but are not limited to, the Internet, corporate intranets, local area networks, mobile communication networks, and combinations thereof.

Communication module 106 may be configured to receive and/or send information (e.g., information pertaining to a medical image, etc.) via a network (e.g., a wired network and/or a wireless network). Examples of the network include wireless networks such as Bluetooth®, WiFi, cellular networks, wireless personal area networks (WPANs), wireless local area networks (WLAN), wireless wide area networks (WWANs), wireless metropolitan area networks (WMAN), etc. In some embodiments, communication module 106 comprises a network interface controller (NIC), which may connect to other networks via a base station or the like and thereby communicate with the Internet. In some embodiments, communication module 106 comprises a radio frequency (RF) module, which is configured to communicate with the Internet wirelessly.

The display device can, for example, be a touch-screen liquid crystal display (LCD). The liquid crystal display may enable the user to interact with the user interface of the terminal 100 (e.g., a mobile terminal). In some embodiments, the display device is controlled to display a user interface with which information pertaining to a medical image and/or a quantitative analysis of a medical image is provided (e.g., a target region, etc.). The display device can be integrated into terminal 100 or operatively connected to terminal 100.

According to various embodiments, terminal 100 includes hardware components (e.g., including circuits), software components (e.g., including computer code stored on computer-readable media), or combinations of both hardware components and software components. Please note that FIG. 1 is merely one example of a particular, specific embodiment with the purpose of presenting the types of components that may exist in the aforesaid computer device (or mobile device).

Various embodiments provide a method for data processing. Data processing may include processing a medical image such as in connection with determining whether the medical image includes an indication of an abnormality or other disease in a captured target organ. In some embodiments, a medical image is processed in connection with performing a quantitative analysis on the medical image. For example, the medical image may be processed to determine one or more target regions (e.g., a lesion region and/or an organ region). Information pertaining to the target region may be provided to a user via a user interface on a terminal. In some embodiments, results of the data processing are provided to a user at a client (e.g., on a user interface of the terminal). The results of the data processing may be generated (e.g., the data processing may be performed) by one or more terminals that are remote to the client at which the results are provided. For example, the data processing may be performed by a server such as a web service.

FIG. 2 is a flowchart of a method for data processing according to various embodiments of the present application.

According to various embodiments, process 200 is implemented by terminal 100 of FIG. 1. Interface 700 of FIG. 7 and/or interface 800 of FIG. 8 may be implemented in connection with process 200.

At 210, a target image is obtained. In some embodiments, the target image is a medical image. In some embodiments, the target image is obtained by a terminal such as a server. As an example, the target image may be uploaded by a user via a client. As another example, the server may obtain the target image directly from equipment that provides medical imaging technology, or from a storage on which the equipment stores the target image. The server may be configured to provide a web service associated with data processing such as image analysis and/or medical diagnostic services.

According to various embodiments, a cloud server receives an image to be recognized (e.g., the target image). In response to receiving the image and/or in response to receiving a request to perform a data analysis with respect to an image such as via a client, the cloud server (or another associated server) may process the image. The image to be recognized may be a processed medical image or a medical image that is to be processed. The processing of the medical image may include masking a first medical image taken of a patient data to obtain a second medical image, and/or applying a filter to the second medical image to obtain the image to be recognized.

The first medical image may correspond to an image of a target organ obtained through a medical imaging technology. For example, the medical imaging technology may be, but is not limited to, X-rays, gamma rays, nuclear magnetic resonance, ultrasound, etc. Various medical imaging technologies may be used for different target organs. The present application imposes no specific restrictions in this regard. The example of a first medical image that is a CT (computed tomography) image is used for the purpose of illustration. The target organ may be an organ in the body of a patient. For example, the organ may be a brain, a heart, or a lung, etc. The patient may be a human patient, an animal, etc.

At 220, a target region image is segmented from the target image. In some embodiments, the target region image comprises a target object region of the target image. A server may process/filter the target image to obtain the target region image. In some embodiments, the target region image is segmented based at least in part on an image analysis (e.g., an analysis that determines/identifies a particular organ within the medical image). The particular type of organ within a medical image may be determined (automatically) based on the image analysis performed with respect to the medical image, or the type of organ may be identified in advance of the image analysis such as via a user interface provided on a client or in connection with a request to perform the processing of the medical image. In some embodiments, a request to perform the processing of the medical image indicates a particular type of segmentation model or image analysis that is to be performed. A web service via which the data processing is performed and/or to which the image is provided may be specifically configured to implement a segmentation model for a particular organ.

As an example, if the target region image is a lung region image, segmenting a target region image from the target image comprises: using a lung segmentation model to segment the lung region image from the target image.

According to various embodiments, an organ specific segmentation model is built based at least on a training of a machine learning model using a deep-learning-based segmentation network. For example, a lung segmentation model (e.g., a segmentation model specific to lungs) may be built based at least in part on using a generative adversarial network to learn prior knowledge of lung information (e.g., information pertaining to a lung such as average shape, average size, average color, etc. and/or statistical information pertaining to characteristics of the lung); while training a deep-learning-based segmentation network, using lung shape information and lung local space pixel information from the learned prior knowledge to build a first loss function; and using the first loss function to guide lung segmentation model learning so as to obtain the lung segmentation model. In some embodiments, the information pertaining to an organ (e.g., the lung information) is mapped to one or more characteristics of the patient such as age, etc. The information pertaining to the organ can comprise ranges that define a normal organ (e.g., an organ that does not include an abnormality or that does not suffer from a disease, etc.) such as a range of sizes, color variation, etc.

As an example, in the case of lungs, the color of a lung generally appears to whiten in CT images of pneumonia. However, the appearance of a whitening of the lung is an extremely poor differentiation between the lung region and surrounding tissues. Because human lung contours are roughly similar (e.g., across patients of a similar profile such as age, etc.), various embodiments include a generative adversarial network that is used to learn prior knowledge of lung shapes. The generative adversarial network may be used to train a machine learning model (e.g., for use in connection with identifying organs from target images, etc.). In connection with training the deep-learning-based segmentation network, the organ information (e.g., the information defining the organ such as the prior shape information and local space pixel information) is used to build a first loss function. The first loss function may be used in connection with guiding the learning of the lung segmentation model. The segmentation model for an organ is based at least in part on information pertaining to organ pathology (e.g., the model is trained using a data set that provides a basis of a pathology associated with the organ). Accordingly, the trained lung segmentation model provides good pathological lung segmentation results.

According to various embodiments, the target region corresponds to the region of possible pathologic change in the target organ. The region of possible pathologic change may correspond to an area of the target organ subject to inflammation or an infected area of the target organ. The region of possible pathologic change may be defined based at least in part on a statistical representation of the target organ (e.g., defined thresholds within a statistically relevant segment of patients, etc.). In some embodiments, the target region corresponds to a specific region that is to be extracted from the target organ. The specific region may correspond to a region that is different (e.g., statistically different such as according to one or more thresholds) from normal organ tissue.

At 230, a target region image is obtained. In some embodiments, the target region image is obtained based at least in part on the use of a machine learning model (e.g., to analyze the target image). As an example, the machine learning model may be specific to the organ being analyzed (e.g., the organ in the medical image). The machine learning model may be selected based at least in part on the organ being analyzed. A server may implement the machine learning model to recognize the target region image. In some embodiments, a recognition result is obtained based at least in part on the use of the machine learning model to analyze the target image.

At 240, a measure of risk that a patient has a target disease is determined. In some embodiments, the measure of risk is obtained by a computer such as a server that performs an analysis of the target image. For example, the measure of risk may be determined based at least in part on the analysis by or use of the machine learning model. The measure of risk may be determined using the target region image (e.g., that is obtained using the machine learning model). In some embodiments, imaging evidence corresponding to a diagnosis for a target disease is determined and/or provided to a patient or care provider. The imaging evidence may include a heat map that indicates or identifies an infected area, etc.

According to various embodiments, the measure of risk that a patient has a target disease includes a probability. The measure of risk may also include a confidence (e.g., confidence interval) with respect to the measure of risk that the patient has the target disease. The measure of risk may comprise one or more probabilities respectively corresponding to different target diseases. The recognition results associated with an analysis or processing of the target image and/or target region image may comprise the measure(s) of risk that the patient has one or more target diseases. The determination of the measure of risk(s) may be based on a training of a model (e.g., a machine learning model) using a set of medical images associated with organs that have a particular target disease and/or a set of medical images associated with organs that do not have the particular disease (e.g., an organ that is operating normally).

According to various embodiments, the recognition results are preset for different target organs. Different target organs can correspond to different recognition results or a set of recognition results. For example, a mapping of recognition results to organs may be defined/stored (e.g., in advance of the obtaining the target region image or analysis of the target image using the machine learning model).

According to various embodiments, the machine learning model may be a trained model, or the machine learning model may be a reinforcement learning model. In embodiments of the present application, the example of a trained model is used for the purpose of illustration. The first machine learning model may employ an "encoder-decoder" structure according to which the output from the encoder network may correspond to an input to both the classification network and the decoder network, such that the classification network and the decoder network operate in parallel. In some embodiments, one or more of both the encoder network and the decoder network use three-dimensional convolutional layers. As an example, both the encoder network and the decoder network use three-dimensional convolutional layers. For example, the machine learning model may be a three-dimensional network model. In some embodiments, the encoder network employs a resnext50 network architecture. The decoder network may include an ASPP structure and upsampling layers, and the classification network may include a series of convolutional layers and global pooling layers. However, the encoder network, the decoder network, and the classification network are not limited to the foregoing.

In some embodiments, recognizing a target region image and obtaining a recognition result based at least in part on using a machine learning model comprises: using a machine learning model to recognize (e.g., analyze) an image to be recognized (e.g., the target image) and recognizing one or more probabilities of being first category targets; and determining the recognition result based at least in part on the probabilities of being a first category as the recognition result. A probability may be determined based on a training of the machine learning model using a sample set of historical information (e.g., if historical sample set comprising 75 out of 100 samples that had a similar feature also had the disease, then the determined probability would be 75%). As an example, the recognition result may correspond to a category associated with a highest probability. As another example, the machine learning model is trained to specifically identify the first category target and returns a probability that the target image comprises the first category target and/or a probability that the target image does not comprise the first category target. To recognize an image may include analyzing the image in connection with determining whether the image has one or more features (e.g., one or more characteristics that may be associated with a disease, etc. such as a statistical association with one or more diseases). In some embodiments, the first category targets include at least one of the following: a first target, a second target, and a third target. The recognition result may comprise a set of probabilities each respectively corresponding to a probability that, of the at least one of the first target, the second target, and the third target, is comprised in the target image. The machine learning model may be a target recognition model, and the machine learning model may be used to recognize the target image (e.g., the image to be recognized). Recognition of the probabilities of being first category targets may include processing (e.g., analyzing) a target image based at least in part on the target recognition model, and determining one or more of (i) a probability that at least part of the target image corresponds to the first target, (ii) a probability that at least part of the target image corresponds to the second target, and (iii) a probability that at least part of the target image corresponds to the third target.

As an example, in the case of a medical image of a lung, the first category targets may correspond to lung diseases, and the recognized (e.g., determined) first category target probabilities may include the probability of atypical pneumonia (e.g., a first target), the probability of common pneumonia (e.g., a second target), and the probability of other lung disease (e.g., a third target). Various categories of targets may be implemented (e.g., defined and identifiable by analysis of an image using the model). Various other targets may be included within each category. For example, the targets included within each category may correspond to targets for which the model has been trained/defined to identify, etc.

In some embodiments, after determining target probabilities for the first category, the target probabilities are stored in association with the target image (e.g., the medical image). For example, the target probabilities may be synchronously transferred to an image filing and communication system. The image filing and communication system may communicate (e.g., synchronously transfer) the recognition result to a report terminal (e.g., a client terminal that provides the recognition results to a user via a user interface)

Figure 3:
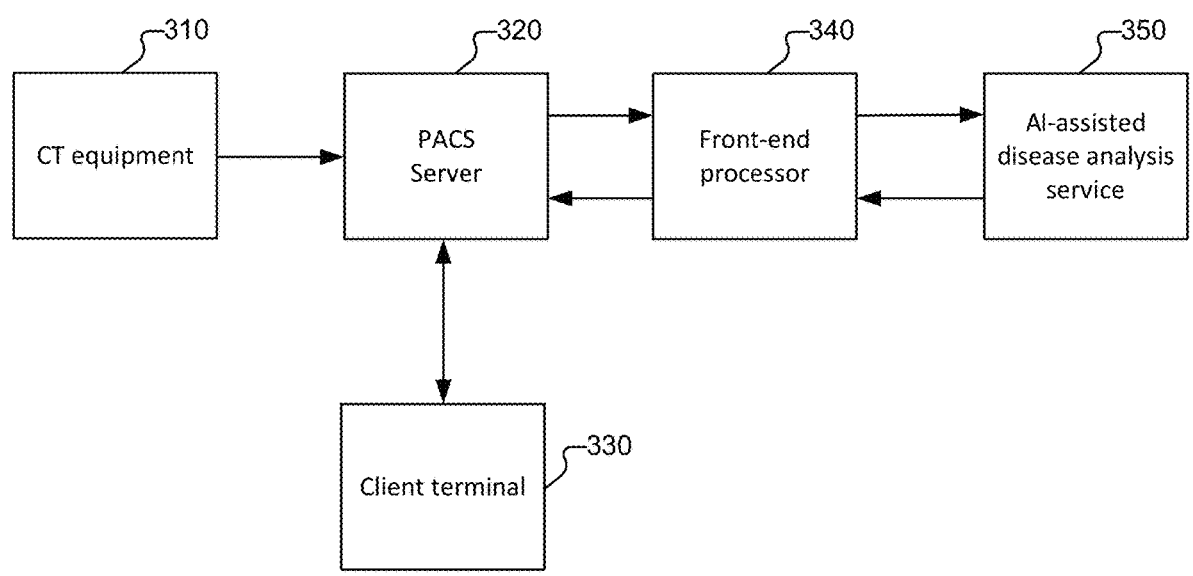
FIG. 3 is a block diagram of devices used in connection with a method for data processing according to various embodiments of the present application.

FIG. 3 is a block diagram of devices used in connection with a method for data processing according to various embodiments of the present application.

According to various embodiments, system 300 implements at least part of process 200 of FIG. 2, process 400 of FIG. 4, process 500 of FIG. 5, process 600 of FIG. 6, interface 700 of FIG. 7, and/or interface 800 of FIG. 8. At least part of system 300 may be implemented by terminal 100 of FIG. 1.

Referring to FIG. 3, system 300 includes CT equipment 310, PACS server 320, client terminal 330, front-end processor 340, and AI-assisted disease diagnostic analysis service 350. Although system 300 is described in the context of a medical imaging technology corresponding to a CT scan, various other medical imaging technologies may be implemented and various types of medical images may be obtained. Accordingly, in some embodiments, CT equipment 310 may correspond to various other imaging technologies.

According to various embodiments, CT equipment 310 performs an imaging of a patient. In connection with the imaging of the patient, CT equipment 310 obtains (e.g., generates) an image such as a medical image. CT equipment 310 may store the image and other information pertaining to the patient and/or imaging of the patient. For example, CT equipment 310 may store the image and such other information locally and/or at a network or remote storage.

After CT equipment 310 completes imaging of the patient, the medical imaging data (e.g., the medical image and/or information pertaining to the patient and/or imaging of the patient) is transmitted to a server such as a Picture Archiving and Communication System (PACS) server 320. PACS server 320 may correspond to an image filing and communication system. PACS server 320 may associate the medical imaging data to an electronic medical record corresponding to the patient. In some embodiments, PACS server 320 stores a database for an electronic medical record system. PACS server 320 may comprise a plurality of servers. PACS server 320 may be connected to a client terminal 330 and/or a front-end processor 340. For example, PACS server 320 may be connected to client terminal 330 and/or front-end processor 340 via one or more networks (e.g., wired, wireless, etc.) or via one or more servers.

Front-end processor 340 may obtain a medical image from PACS server 320. In some embodiments, front-end processor 340 obtains the medical image from PACS server 320 in response to a request to process and/or analyze the medical image. For example, a user may input a request to process and/or analyze the medical image via a user interface provided on client terminal 330. Front-end processor 340 may be configured to process the medical image. For example, front-end processor 340 may perform data masking, data filtering, and other such tasks on the captured medical images. In some embodiments, the front-end processor 340 processes the medical image in response to CT equipment 310 performing the medical imaging. In some embodiments, after front-end processor 340 completes data masking, data filtering, and other such tasks on the captured medical images, front-end processor 340 provides the processed medical image data to one or more terminals such as a server corresponding to a public cloud. For example, front-end processor 340 may communicate the processed medical image to a server corresponding to a public cloud (e.g., a server associated with a web service).

An analysis of the processed medical image may be triggered after front-end processor 340 processes the medical image. For example, in response to front-end processor 340 providing the medical image to the public cloud, AI-assisted disease diagnostic analysis service 350 is triggered (e.g., invoked). As another example, AI-assisted disease diagnostic analysis service 350 is triggered (e.g., invoked) in response to a request being received from a user via a user interface provided by client terminal 330. According to various embodiments, in response to a triggering, AI-assisted disease diagnostic analysis service 350 is caused to perform an analysis with respect to the medical image. In some embodiments, in response to a triggering, AI-assisted disease diagnostic analysis service 350 provides a result of an analysis of the medical image (e.g., an indication of the measure of risk that a patient has one or more diseases, etc.).

According to various embodiments, AI-assisted disease diagnostic analysis service 350 provides a response including information pertaining to an analysis of the medical image (e.g., a recognition result). AI-assisted disease diagnostic analysis service 350 may provide the response after obtaining the recognized first category target probability (or probabilities). The AI-assisted disease diagnostic analysis service 350 may provide the response to front-end processor 340. In response to AI-assisted disease diagnostic analysis service 350 providing the response (e.g., the recognition result from the AI-assisted disease diagnostic analysis service 350), front-end processor 340 obtains the recognition result and front-end processor 340 may transfer (e.g., synchronously transfer) the recognition result to PACS server 320. In some embodiments, the recognition result is stored in association with the medical image. For example, in response to receiving the recognition result (e.g., from front-end processor 340), PACS server 320 may store the recognition result in association with (e.g., mapped to) the corresponding medical image. The information communicated by the AI-assisted disease diagnostic analysis service 350 pertaining to the recognition result may further include an indication of the medical image to which the recognition result corresponds (e.g., an identifier of the medical image, an identifier of the patient, etc.).

According to various embodiments, PACS server 320 provides (e.g., synchronously communicates) the recognition result to client terminal 330. For example, the PACS server 320 communicates the recognition result to the client terminal so that the physician may quickly obtain the recognition result. In some embodiments, the PACS server 320 provides an indication to client terminal 330 that a recognition result is available (e.g., rather than sending the recognition result). For example, client terminal 330 may access the recognition result and/or medical image via a web service. In some embodiments, the communicating the recognition result comprises sending an email to a user (e.g., a physician) with the recognition result or an indication that a result is available for access. In some embodiments, the communicating the recognition result comprises sending a notification to a user of a web service in an application with which the web service is provided.

The physician or other care provider may quickly determine (e.g., obtain) a therapeutic regimen corresponding to the first category target (e.g., if the recognition result indicates that the medical image is indicative of the presence of a corresponding disease). The therapeutic regimen corresponding to the first category target may be obtained from the imaging analysis results and corresponding therapeutic regimens stored in a database such as a database of a hospital or a database hosted in connection with a web service. According to various embodiments, the database stores a mapping of imaging analysis results (e.g., recognition results, measures of risk, etc.) to therapeutic regimens. If one type of imaging analysis result corresponds to multiple therapeutic regimens, the physician or other care provider may screen the multiple therapeutic regimens to select the one suited to the patient. For example, an application with which the physician or other care provider views the imaging analysis result and/or therapeutic regimens may include a filtering function that can filter multiple therapeutic regimens according to one or more characteristics of the patient (e.g., age, medical history, prescriptions, allergies, medical insurance provider, etc.). In some embodiments, a web service analyzes the imaging analysis result, corresponding therapeutic regimen(s), and/or the one or more characteristics of the patient, and the web service provides a recommendation to the physician or other care provider. In some embodiments, the physician or other care provider may edit the therapeutic regimen to customize the therapeutic regimen to a condition of the applicable patient. The physician or other care provider may edit the therapeutic regimen via one or more inputs to the client terminal 330. An application running on the client terminal 330 or a web service hosted by a service may edit the therapeutic regimen based at least in part on the one or more inputs that are input by the physician or other care provider.

The work efficiency of the physician or other care provider can be increased through the embodiments described herein. In addition, the accuracy of disease diagnosis and development of a therapeutic regimen for the patient may be improved. Practice has proven that the above scheme provides a tremendous advantage in terms of screening speed and accuracy, far superior to manual image reading by the vast majority of physicians. Moreover, as deep learning continues, image reading accuracy will continue to improve. In addition to reducing burdens on radiologists and/or other care providers, various embodiments improve diagnostic and therapeutic efficiency. The data processing method provided by various embodiments assists physicians and/or other care providers in making precise assessments concerning multiple kinds of specific diseases such as pulmonary pneumonia, pulmonary emphysema, and lung cancer. Various other diseases may be analyzed and/or identified. Various embodiments use deep learning in connection with continued increase of recognition categories and quality. Various embodiments may remedy current deficiencies in basic medical service capabilities and provide technical support for raising the quality of diagnosis in hospitals (e.g., basic-level hospitals) on a broad scale. The data processing method provided by various embodiments of the application improves the image-reading efficiency and convenience of physicians and/or other care providers without affecting the workflow of existing systems in hospital imaging departments. Various embodiments thus greatly increase physician work efficiency.

According to various embodiments, a machine learning model analyzes (e.g., automatically recognizes or analyzes) images. The recognition of images (e.g., medical images) based at least in part on the machine learning model comprises receiving an image to be recognized (e.g., a target image); segmenting a target region image from the target image, wherein the target region image comprises a target object region in the target image; using the machine learning model to determine (e.g., recognize) the target region image; and obtaining a recognition result (e.g., a measure of risk) based at least in part on the target region image. The use of a machine learning model in connection with analyzing a medical image attains the goal of automatic image analysis and recognition and thereby increases image analysis efficiency. Various embodiments solve the technical problem of lower efficiency of image analysis in the related art.

Currently, precision of lesion segmentation according to current schemes is relatively poor and schemes according to related art result in inaccurate segmentation of lesion regions. Accordingly, more accurate segmentation results is not possible according to current schemes. Various embodiments of data processing solve the foregoing problem(s) with the current schemes. Various embodiments include implementation of a machine learning model. The machine learning model may be a lesion segmentation model. In some embodiments, the use of a lesion segmentation model in connection with analyzing an image (e.g., a medical image) includes segmenting a lesion in the target image based at least in part on the lesion segmentation model, and determining the location and size of the lesion (e.g., the lesion identified based on analysis of the target image). According to various embodiments, the target image is annotated with (or associated with) information pertaining to the lesion. In some embodiments, a label at the lesion location is added (e.g., to the target image). Characteristics pertaining to the lesion may be determined. For example, a volume of the lesion in proportion to the target image may be determined (e.g., computed). The volume of the lesion may be determined based on the lesion size (e.g., a size of the lesion in comparison/proportion to the target image or the organ within the target image). The volume of the lesion in proportion to the target image may be deemed the recognition result. As another example, a color, shape, location, etc. of the lesion may be determined.

Various embodiments, including quantitative analysis of the lesion, are used to help a physician to better diagnose and treat a disease of a patient. Labelling the lesion location and determining (and providing) the characteristics of the lesion such as the volume of the lesion in proportion to the target region image (or the target organ) may help the physician or other care provider to more quickly obtain or determine data on the disease of the patient.

FIG. 4 is a block diagram of a method for data processing according to various embodiments of the present application.

According to various embodiments, process 400 is implemented by terminal 100 of FIG. 1. Interface 700 of FIG. 7 and/or interface 800 of FIG. 8 may be implemented in connection with process 400. Process 400 may be implemented in connection with system 300 of FIG. 3.

As illustrated in FIG. 4, CT image 410 (e.g., corresponding to the aforementioned medical image) is obtained based at least in part on implementing a medical imaging technology such as the use of CT equipment (e.g., such as CT equipment 310 of FIG. 3). After the CT equipment completes imaging the patient (e.g., at least a target organ of the patient), the CT image 410 may be obtained and stored. As an example, if the target organ is a lung, a lung disease lesion segmentation model may be used to segment the lung region image. In some embodiments, the lung disease lesion segmentation model may be used in connection with identifying and/or labelling characteristics of the lesion such as the location, volume, size, etc. of the lesion. A lesion or location of the lesion may be labelled (e.g., on the target image or the target region image) and the volume proportion of the lesion in the target region image may be determined.

In some embodiments, the lesion segmentation model (e.g., a lung lesion segmentation model such as lung lesion segmentation model 440 of FIG. 4) may be a trained model or a reinforcement learning model. The lung segmentation model accurately segments lesions in the target image. According to various embodiments, the lesion segmentation model is built (e.g., determined) based at least in part on building a multi-task, deep-learning network to learn lesion classification; using an encoding module to extract underlying features from a target organ in historical medical images; using the extracted underlying features to build a classification task; and building a second loss function with the classification task. In some embodiments, the classification task is the task of classifying lesions in the target organ. According to various embodiments, the second loss function is used in connection with guiding (e.g., informing) the learning of the lesion segmentation model so as to obtain the lesion segmentation model.

In some embodiments, after the machine learning model is used to analyze the target region image and obtain a recognition result, the recognition result is communicated to a client terminal (e.g., client terminal 330 of FIG. 3), and a prompt message is triggered. The triggering the prompt message may include causing a user interface on the client terminal to provide an indication of a message and/or prompting a user of the client terminal to view the results of the image analysis. The prompt message may be a prompt to a user of the client terminal to check the recognition result without delay, or it could trigger an alert prompt based at least in part on information in the recognition result.

As illustrated in FIG. 4, according to various embodiments, the CT image (e.g., the target image) is analyzed/processed based at least in part on the lung image segmentation model 420. For example, the lung image segmentation model 420 may be used in connection with segmenting a target region (e.g., a target region image) from CT image 410. In response to segmenting the target region, the corresponding target region may be processed based at least in part on a disease recognition model 430 and/or a lung lesion segmentation model 440. In some embodiments, the target region image is analyzed based at least in part on the disease recognition model 430 in connection with determining whether the CT image is indicative of the patient having a disease (e.g., a disease specific to the model or any disease that is identifiable using the model), and/or one or more properties of the disease. In the case of the organ being a lung, in some embodiments, the target region image is analyzed based at least in part on the lung lesion segmentation model 440. The lung lesion segmentation model 440 may identify and/or segment the lung lesion from the target region image. In some embodiments, the lung lesion segmentation model 440 is used in connection with characterizing a lesion comprised in the target region image (e.g., determining one or more characteristics associated with the lesion).

FIG. 5 is a diagram of a method for data processing according to various embodiments of the present application.

According to various embodiments, process 500 is implemented by terminal 100 of FIG. 1. Interface 700 of FIG. 7 and/or interface 800 of FIG. 8 may be implemented in connection with process 500. Process 500 may be implemented in connection with system 300 of FIG. 3 and/or process 400 of FIG. 4. At least part of process 500 may be implemented by one or more servers such as a cloud server.

Using a CT image of a lung as an example, a detailed description of various embodiments of the present application with reference to FIG. 5 is provided. In response to a CT image of a patient being acquired, the CT image may be input into the lung segmentation model. In some embodiments, the lung segmentation model may include an encoder network, a recognition network, and/or a decoder network. For example, the lung segmentation model may employ an "encoder-decoder" structure and the output from the encoder network may correspond to an input to both the recognition network and the decoder network, such that the recognition network (e.g., classification network) and the decoder network operate in parallel. In some embodiments, one or more of the encoder network and the decoder network use three-dimensional convolutional layers. As an example, both the encoder network and the decoder network use three-dimensional convolutional layers. For example, the first machine learning model may be a three-dimensional network model. In some embodiments, the encoder network employs a resnext50 network architecture. The decoder network may include an ASPP structure and upsampling layers, and the recognition network (e.g., the classification network) may include a series of convolutional layers and global pooling layers. However, the encoder network, the decoder network, and the recognition network are not limited to the foregoing.

In response to the CT image being input to the lung segmentation model, the CT image may be processed based at least in part on the encoder network. For example, the encoder network extracts and processes the CT image. The encoder network may extract target region features from the CT image. After obtaining the target region features, the recognition network may be used to process the target region features and to obtain an image recognition result. After obtaining the target region features, the decoder network may be used to process the target region features and to extract an image of the target region. The processing of the target region features and the extraction of the image of the target region may assist the physician and/or other care provider to quickly determine the condition of the patient and to facilitate the physician and/or other care provider in performing early intervention and treatment to prevent the condition of the patient from becoming serious or even critical, thus lowering the fatality rate. In addition, various embodiments may be implemented as a public cloud-based deployment scheme. As such, the method and system for processing a medical image is convenient, fast, and flexible. In some embodiments, no manual triggering is required throughout the analysis process. Various embodiments may be quickly deployed within a hospital and are highly efficient.

According to various embodiments, after obtaining a first image of the target region in the medical image (e.g., the target region image), the image analysis comprises: using a second machine learning model to process the medical image and obtain a second image of the target organ. The second machine learning model includes obtaining the medical image, inputting the medical image into a lesion segmentation module, and obtaining an image of the lesion and/or target organ. In some embodiments, the lesion segmentation module processes the medical image, including inputting the medical image into an encoder network, obtaining feature information pertaining to the lesion, and inputting the feature information pertaining to the lesion into a decoder network to obtain the image of the lesion and to obtain a proportion of the target region (e.g., the lesion) in the target organ based at least in part on the medical image and the image of the lesion.

According to various embodiments, a medical image analysis system is provided in connection with implementing the data processing and/or image analysis described herein. The system may include medical imaging equipment (e.g., CT equipment) configured to capture a first medical image of a patient. The system may include a front-end processor configured to perform a data masking on the first medical image to obtain a second medical image, and to process the second medical image based at least in part on data filtering to obtain an image to be recognized (e.g., the target image), and to provide the image to be recognized to an analysis device. The system may include an analysis device configured to receive the image to be recognized (e.g., the target image), segment a target region image from the image to be recognized, and to use a machine learning model in connection with analyzing the target region image and obtaining a recognition result. The target region image may include a target object region in the image to be recognized.

In some embodiments, the analysis device of the system is further configured to synchronously communicate the recognition result to an image filing and communication system (e.g., a server), and/or provide the recognition result to a client terminal and cause a prompt message to be communicated (e.g., a prompt message to be displayed on a user interface of the client terminal).

FIG. 6 is a flowchart of a method for data processing according to various embodiments of the present application.

According to various embodiments, process 600 is implemented by terminal 100 of FIG. 1. Interface 700 of FIG. 7 and/or interface 800 of FIG. 8 may be implemented in connection with process 600.

At 610, a target image is obtained. In some embodiments, the target image is a medical image. In some embodiments, the target image is obtained by a terminal such as a server. As an example, the target image may be uploaded by a user via a client. As another example, the server may obtain the target image directly from equipment that provides medical imaging technology, or from a storage on which the equipment stores the target image. The server may be configured to provide a web service associated with data processing such as image analysis and/or medical diagnostic services.

In some embodiments, the target image is obtained based at least in part on a user selection or preference. For example, a user may input a selection to a user interface provided in a client terminal. The user may browse a file system storing one or more images (e.g., medical images), and the user may select the target image from a target image source. The target image source may be a database pertaining to medical images (e.g., captured by medical imaging equipment) such as a database for electronic medical records.

According to various embodiments, the user is a patient, a physician, or other care provider that is to view medical images in connection with providing medical services (e.g., diagnostic services, treatment services, etc.) to a patient. In some implementations, the user may an individual having various other roles.

The target image source may be medical images of a target organ obtained through a medical imaging technology. The target organ may be a human organ in the body of a patient. For example, it may be a brain, a heart, or a lung, etc. The patient may be a human patient, an animal, etc. The medical imaging technology may be, but is not limited to, X-rays, gamma rays, nuclear magnetic resonance, or ultrasound. Various other medical imaging technologies may be implemented.

At 620, a target image analysis process is selected. In some embodiments, the target image analysis process is a process by which the data source is to be analyzed (e.g., a selection of a quantitative analysis to be performed on the first medical image). The target process may be selected based at least in part on one or more inputs by a user, such as an input to a user interface.

The target image analysis process may correspond to a processing algorithm or method. The target image analysis process may be selected from among multiple analysis processes (e.g., processing algorithms) provided by the system. Different analysis processes (e.g., processing algorithms) may be provided in advance for medical images obtained with different imaging technologies. For example, a mapping of analysis processes to imaging technologies may be stored. A group of analysis processes corresponding to an imaging technology may be determined based on the mapping of analysis processes to imaging technologies. In response to a determination of an image technology used in connection with capturing the medical image (e.g., the data source), at least a subset of the group of analysis processes is provided to the user to enable the user to select the target process from among the subset of the group of analysis processes. The analysis processes may include existing processes for analyzing an image captured from a particular imaging technology. Different analysis processes may have different processing times, accuracies, etc.

At 630, the target image is processed based at least in part on the target image analysis process. For example, the target image analysis process is used to process the target image (e.g., image to be recognized). A recognition result corresponding to the target image (e.g., the image to be recognized) and/or target data in the target image may be obtained based at least in part on the processing of the target image using the target image analysis process. The target image analysis process may include calling (e.g., invoking) a target machine learning model to process the target image in connection with obtaining the recognition result and/or the target data.

According to various embodiments, the target machine learning model is a trained model, or a reinforcement learning model. In embodiments of the present application, the example of a trained model is used for the purpose of illustration. The target machine learning model may use an "encoder-decoder" structure and may connect after the encoder network to a classification network (e.g., a recognition network) which is parallel to the decoder network. For example, the network model may employ an "encoder-decoder" structure and the output from the encoder network may correspond to an input to both the classification network and the decoder network, such that the classification network and the decoder network operate in parallel. In some embodiments, one or more of the encoder network and the decoder network may make use of three-dimensional convolutional layers. As an example, both the encoder network and the decoder network use three-dimensional convolutional layers. For example, the target machine learning model may be a three-dimensional network model. In some embodiments, the encoder network employs a resnext50 network architecture. The decoder network may include an ASPP structure and upsampling layers, and the classification network may include a series of convolutional layers and global pooling layers. However, the encoder network, the decoder network, and the classification network are not limited to the foregoing.

At 640, a recognition result and/or target data is provided. In some embodiments, the recognition result and the target data are provided via a graphical user interface of a terminal. The recognition result and the target data may be provided to a user such as a patient, a physician or other care provider, etc.

According to various embodiments, the recognition result includes one or more recognized first category target probabilities. In the case of a medical image of a lung, the first category target may be lung disease, and the recognition of first category probabilities may include, but is not limited to, the probability of atypical pneumonia, the probability of common pneumonia, and the probability of other lung disease. Various other probabilities may be computed and/or provided, and various other categories of disease may be implemented such as categories determined based at least in part on the target organ to be analyzed.

According to various embodiments, the target data includes the volume proportion of the lesion in the target image. Various embodiments include a quantitative analysis of the lesion to help the physician in providing better diagnosis and treatment of the disease of the patient.

Various embodiments include an interface provided to the user in connection with selecting/invoking an image analysis to be performed with respect to a target image and/or to view results of the image analysis (e.g., to display recognition results and/or target data).

FIG. 7 is a diagram of an interface used in connection with processing an image according to various embodiments of the present application.

According to various embodiments, interface 700 is implemented by terminal 100 of FIG. 1. Interface 700 may be implemented in connection with at least part of process 200 of FIG. 2, process 400 of FIG. 4, process 500 of FIG. 5, process 600 of FIG. 6, and/or interface 800 of FIG. 8.

As illustrated in FIG. 7, interface 700 may include an area 720 in which a medical image may be input (or selected) and/or a results display area 750. Interface 700 may include selectable element 730 and/or element 740 that upon selection of such invokes one or more functions or processes to be performed. Element 730 may correspond to a quantitative processing (e.g., to invoke a processing of the medical image/target image). Element 740 may correspond to an image comparison (e.g., to invoke a comparison between two medical images). In some embodiments, element 740 corresponds to a function that invokes performing an image analysis or to obtain results of an image analysis such as a measure of risk pertaining to a disease of the patient, etc.

In some embodiments, the medical image (e.g., the target image) is obtained via user interaction with (e.g., user inputs with respect to) the area 720. As an example, interface 700 may include one or more selectable elements with respect to which a user may select a medical image or a function to be performed with respect to a medical image. In some embodiments, interface 700 includes element 710 that is configured to, in response to selection via a user input, facilitate a user to upload a medical image. As an example, in response to selection of element 710, another interface or window (e.g., a floating element) may be displayed that allows a user to browse a file system to select a desired medical image. As another example, in response to selection of element 710, another interface or window (e.g., a floating element) may be displayed that provides the user a set of a plurality of images from which the user selects a desired medical image. According to various embodiments, the user may select the medical image in need of uploading by clicking on "Upload Medical Image" (e.g., element 710), or the user may directly drag the medical image file to within the box bordered by the dashed line (e.g., area 720) to achieve the objective of uploading the medical image.

According to various embodiments, the classification result (e.g., the recognition result) and/or the target region image is displayed in the results display area 750. Target data may be displayed in results display area 750. As an example, the results display area 750 may be displayed on the right side for user viewing convenience. Interface 700 may display information pertaining to the patient and results display area 750 to assist the user (e.g., a physician or care provider) with conveniently accessing and viewing the medical image (e.g., a part of the medical image such as the target organ or the target region), and/or information pertaining to the quantitative analysis of the medical image.

Let us take the example of a user who is a physician for the purpose of illustration. After acquiring a patient's medical image, the physician may upload the medical image and view the classification result and target region displayed in the display area. The physician thus can determine the patient's condition and provide treatment suggestions based on the classification result and target region.

As an example, in the case that the user is a patient, after the user obtains the medical image for the patient, the patient may upload the medical image (e.g., to area 720 of the interface 700 of FIG. 7) and view the recognition result and target data displayed in the display area (e.g., area 750 of the interface 700 of FIG. 7). Thus, the patient may gain a certain understanding of the patient's own condition and, on the basis thereof, may promptly go to the hospital for treatment. Interface 700 empowers patients to view results of the diagnostic test (e.g., CT scan) and to obtain certain information pertaining to a classification of an anomaly/disease (or lack thereof) within the results of the diagnostic test. Similarly, care providers (e.g., physicians) may use interface 700 to quickly view results of a quantitative analysis (e.g., the classification results, image of the target region, and/or information pertaining to a deformation relationship over a set of medical images, etc.).

FIG. 8 is a diagram of an interface used in connection with processing an image according to various embodiments of the present application.

According to various embodiments, interface 800 is implemented by terminal 100 of FIG. 1. Interface 800 may be implemented in connection with at least part of process 200 of FIG. 2, process 400 of FIG. 4, process 500 of FIG. 5, process 600 of FIG. 6, and/or interface 700 of FIG. 7.

As illustrated in FIG. 8, interface 800 may include an area 810 (e.g., data source selection area) in which a data source is input (or selected) and/or a results display area 880. Interface 800 may also include an area 840 (e.g., a process selection area) within which a target process is selected (e.g., via one or more inputs).

Interface 800 may include selectable element 820 and/or element 830 with which one or more data sources may be selected. Selection of element 820 and/or 830 may provide to a user a set of medical images from which the data source is selected. As an example, in response to selection of element 820 and/or element 830, a file system may be accessed and/or provided to the user to navigate to a directory in which the data source is stored. In some embodiments, selection of the data source(s) includes a user dragging and dropping one or more medical images to the data source selection area (e.g., area 810) such as dragging a medical image over the element 820 and/or 830. Element 830 may correspond to an area in which (or an element with which) a quantitative processing is selected or determined (e.g., with which an input may be input to invoke a processing of the medical image). Element 840 may correspond to an area in which (or an element with which) an image comparison is selected or determined (e.g., with which an input may be input to invoke a comparison between two medical images). In some embodiments, element 840 corresponds to a function that invokes performing an image analysis or to obtain results of an image analysis such as a measure of risk pertaining to a disease of the patient, etc.

According to various embodiments, interface 800 is provided to a user, and the user may select the to-be-processed target image source from the image source selection area, and the storage location and specific type of the image to be recognized selected by the user may be displayed in this area. In response to selection of the image to be recognized (e.g., the target image), the user may then view in the process selection area at least one process matching the image to be recognized. Specifically, the user may view the name, processing time, price, and other information relating to the image analysis process and may select the image analysis suited to the user's needs and thereby obtain the target image analysis process. For example, in response to selection of the data source, a group of analysis processes corresponding to the data source (e.g., the target image) may be determined. The determining the group of analysis processes corresponding to the data source may include determining an imaging technology associated with the data source, and determining the group of analysis processes based at least in part on the imaging technology. For example, a mapping of analysis processes to imaging technologies may be stored. A group of analysis processes corresponding to an imaging technology may be determined based on the mapping of analysis processes to imaging technologies. In response to a determination of an image technology used in connection with capturing the medical image (e.g., the data source), at least a subset of the group of analysis processes is provided to the user to enable the user to select the target process from among the subset of the group of analysis processes. The at least subset of the group of analysis processes may be provided to the user via the process selection area 840. In some embodiments, providing the at least subset of the group of analysis processes includes providing an indication of a name 860, a processing time, a location 850, a price 870, and other information relating to the corresponding analysis process(es). In some embodiments, the subset of the analysis processes is provided in a drop-down menu within the process selection area 840. In some embodiments, the subset of the analysis processes is provided with corresponding radial buttons. In response to selection of an analysis process via the drop-down menu or the radial button, the process selection area may be updated to reflect the corresponding name of the analysis process, a processing time, a price, and other information relating to the corresponding analysis process. The user may select the analysis process that is suited to the user's needs and thereby obtain the target process.

In response to the selection of the target process, the target process selected by the user is used to process the data source. Results from processing the data source (e.g., the medical image) may be provided in the results display area 880. In some embodiments, the data source and the results from the analysis thereof are provided in the results display area 880.

In some embodiments, the determining a target process selected by the user comprises: obtaining at least one analysis process corresponding to the data type of the target image source (e.g., the data source); providing at least one analysis process (e.g., an indication of the analysis process); receiving a selection input by the user (e.g., to interface 800); and in response to the selection input from the user, determining the target process from among at least one analysis process based at least in part on the selection input.

Different analysis processes may be set up (e.g., defined) in advance for different types of image sources. For example, to use medical image classification and segmentation as an illustrative example, a traditional, features-based extraction method or a two-dimensional neural network image segmentation method may be provided. A processing method corresponding to the target machine learning model provided by embodiments of the present application may also be provided.

The selection input (e.g., corresponding to selection of the target process) may be a click signal generated by the user clicking on an analysis process. In some embodiments, in response to obtaining the click signal, the analysis process corresponding to the click signal (e.g., clicked on by the user based on the click position) may be determined, and the target process is correspondingly obtained.

In some embodiments, processing information for an analysis process is provided. The processing information includes at least one of the following: a processing device, a processing time, and a resource transfer amount. The user may make a selection of the target process based at least in part on the processing information.

Processing devices (e.g., used to perform the target process) may include local devices and cloud devices. The processing time may be the time needed for the analysis process to process the data source and produce the corresponding result for the user. The resource transfer amount may refer to the price to be paid to use the processing algorithm to process the data source.

For the convenience of different users, according to various embodiments, a user may be provided with selection options tailored for different analysis processes. For example, in the case of local devices versus cloud devices, local device analysis processes options are limited, and such analysis processes may have limited processing precision. Therefore, the price for a processing algorithm executed on a local device may be lower, and the price of a processing algorithm executed on a cloud device may be higher. As another example, the processing times of different analysis processes may vary. Thus, a corresponding price may be higher for analysis processes having shorter processing times According to various embodiments, the target machine learning model is obtained by training the target machine learning model by alternating between use of multiple first training samples and multiple second training samples. Each first training sample may include data, a classification label for the data, and label information for target data within the data, and each second training sample comprises data and a classification label for the data.

Medical images in first training data and second training data described above may be masked data collected through various channels, such as hospitals and picture archiving and communication systems (PACS) companies to enhance the training results. Each medical image may be manually assigned a classification label in accordance with the different medical conditions, and target regions may likewise be labeled.

The memory may be for storing app software programs and modules, such as program instructions/modules corresponding to data processing methods and means in embodiments of the present invention. By running software programs and modules stored in the memory, the processors execute various functional apps and data processing. That is, they implement application program data processing methods as described above. The memory may comprise high-speed random access memory. It may further comprise non-volatile memory, such as one or more magnetic storage devices, flash memory, or other non-volatile solid-state memory. In some embodiments, the memory may further comprise memory that is remotely disposed relative to the processor. Such remote memory may be connected to the terminal A via a network. Examples of the network described above include, but are not limited to, the Internet, corporate intranets, local area networks, mobile communication networks, and combinations thereof.

The processor may further, via a communication module, call information and applications stored in memory to execute the steps below: prior to using a machine learning model to recognize the target region image and obtain a recognition result, the method further comprises: building a multi-task, deep-learning network to learn lesion classification; using an encoding module to extract underlying features from a target organ in historical medical images; using the extracted underlying features to build a classification task, wherein the classification task is the task of classifying lesions in the target organ; building a second loss function with the classification task; and using the second loss function to guide the learning of the lesion segmentation model so as to obtain the lesion segmentation model.

Various embodiments described above may be implemented through programs instructing computer terminal-related hardware. The programs may be stored in computer-readable storage media, and the storage media may comprise flash drives, read-only memory (ROM), random access memory (RAM), magnetic disks, or optical disks.

Various embodiments provide a storage medium. In some embodiments, the storage medium is configured to save the program code executed by the methods described herein.

In some embodiments, the storage medium may be located on any computer within a computer terminal group in a computer network or on any mobile terminal within a mobile terminal group.

Although various embodiments described above have been presented as a series of a combination of actions in order to simplify the description, the present application is not limited by the action sequences that are described. Some of the steps may make use of another sequence or be implemented simultaneously in accordance with the present application. Furthermore, certain ones of the actions and modules described in connection with the various embodiments are not necessarily required by the present application.

Through descriptions of the above implementations, various embodiments may be implemented using software and a general-use hardware platform. Hardware may be used to implement various embodiments, including process 200 of FIG. 2, system 300 of FIG. 3, process 400 of FIG. 4, process 500 of FIG. 5, process 600 of FIG. 6, interface 700 of FIG. 7, and/or interface 800 of FIG. 8. Computer software products used in connection with implementing various embodiments may be stored on storage media (such as ROM/RAM, magnetic disks, and optical disks) and include a certain number of instructions used to cause a piece of terminal equipment (which could be a mobile telephone, a computer, a server, or network equipment) to execute the methods described in the embodiments of the present application.

Please understand that, in several embodiments provided by the present application, the disclosed technical content may be implemented in other ways. The means embodiments described above are merely illustrative. For example, the division into units is merely a division by logical function. When actually implemented, there may be other forms of division. For example, multiple units or components may be combined or integrated into another system, or some features might be omitted or not executed. Also, couplings or direct couplings or communication connections between things that are displayed or discussed may be through some interfaces. Indirect couplings or communication connections between units or modules may be electrical or otherwise.

Units as separate components may or may not be physically separate, and components displayed as units may or may not be physical units. They can be located in one place, or they can be distributed across multiple network units. The embodiment schemes of the present embodiments can be realized by selecting part or all of the units in accordance with actual need.

In addition, all the functional units in the various embodiments of the present invention could be integrated in a processing unit. Or each unit could physically exist on its own, or two or three or more units could be integrated into one unit. The integrated units described above may be implemented in the form of hardware, or they may be implemented in the form of software functional units.

If an integrated unit is implemented in the form of software functional units for sale or use as independent products, they may be stored in a computer-readable storage medium. With such an understanding, it becomes clear that the technical schemes of the present invention, whether intrinsically or through those portions that contribute to the prior art, or as all or part of the technical schemes, may be embodied in the form of software products. These computer software products are stored in a storage medium and comprise some instructions for causing a computer device (which could be a personal computer, a server, or a network device) to execute all or some of the steps in the methods in the various embodiments of the present invention. The storage medium described above encompasses: USB flash drives, read-only memory (ROM), random access memory (RAM), mobile hard drives, magnetic or optical disks, or various other media that can store program code.

The above are merely preferred embodiments of the present invention. Please note that persons with ordinary skill in the art could also make certain improvements and embellishments and that these improvements and embellishments should also be regarded as being within the protective scope of the present invention, so long as they do not depart from the principles of the present invention.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method, comprising:
   obtaining, by one or more processors, a target image;
   determining a target image source;
   selecting a target classification process based at least in part on the target image source, the target classification process comprising:
      segmenting, by the one or more processors, a target region image from the target image, wherein:
         the target region image is segmented from the target image based at least in part on a use of a segmentation model;
         the segmentation model is trained using a machine learning process; and
         the target region image comprises a target object region in the target image, the target object region being identified using the segmentation model;
      analyzing, by the one or more processors, the target region image based at least in part on an organ lesion segmentation model to identify a lesion comprised in the target object region, wherein the organ lesion segmentation model is selected based at least in part on an organ comprised in the target object region, and the organ lesion segmentation model is a machine learning model; and
      analyzing, by the one or more processors, the target region image based at least in part on a disease recognition model to determine whether a patient associated with the target image has a disease or other abnormality, and classify any disease or abnormality afflicting the patient; and
   providing an image of the lesion and an indication of whether the patient has a particular disease or abnormality.

2. The method of claim 1, wherein classifying the disease or abnormality comprises:
   determining one or more probabilities corresponding to one or more first category targets based at least in part on the analysis of the target region image; and
   determining the disease or abnormality based at least in part on the one or more probabilities corresponding to the one or more first category targets.

3. The method of claim 2, wherein the one or more probabilities corresponding to the one or more first category targets are one or more probabilities that a patient has one or more diseases according to an image analysis of the target image.

4. The method of claim 2, wherein:
   the first category targets include at least one of the following: a first target, a second target, and a third target; and
   determining the one or more probabilities corresponding to the one or more first category targets comprises:
      analyzing the target image based at least in part on the target recognition model, and determining a probability of a lesion in the target image being the first target, a probability of the lesion being the second target, and a probability of the lesion being the third target based on an analysis of the target image and the target recognition model.

5. The method of claim 4, wherein the target recognition model is trained or defined based at least in part on a set of training images, and at least a subset of the set of training images comprises images corresponding to a target organ subject to a disease associated with the first target, a disease associated with the second target, and a disease associated with the third target.

6. The method of claim 1, wherein:
   identifying the lesion comprised in the target object region comprises:
   segmenting the lesion in the target image based at least in part on the organ lesion segmentation model;
   determining a location of the lesion and size of the lesion based at least in part on the lesion segmentation model;
   adding a label to the location of the lesion and determining a volume proportion of the lesion in the target image based at least in part on the size of the lesion; and
   determining the recognition result based at least in part on the volume proportion of the lesion.

7. The method of claim 6, further comprising:
   building, by the one or more processors, a multi-task, deep-learning network to learn lesion classification;
   using an encoding module to extract underlying features from a target organ in a set of historical medical images;
   building a classification task based at least in part on the extracted underlying features, wherein the classification task corresponds to a task of classifying lesions in the target organ;
   building a loss function based at least in part on the classification task; and
   obtaining the organ lesion segmentation model based at least in part on a training using the loss function.

8. The method of claim 1, wherein providing an image of the lesion and the indication of whether the patient has the particular disease or abnormality comprises:
   providing image of the lesion and the indication to a client terminal; and
   causing the client terminal to provide a prompt message indicating the image of the lesion and the indication is available for viewing.

9. The method of claim 1, further comprising:
   performing data masking with respect to a first medical image of a patient and obtaining a second medical image; and
   performing data filtering with respect to the second medical image and obtaining the target image.

10. The method of claim 1, wherein:
    the target region image is a lung region image; and
    segmenting the target region image from the target image comprises:
    using the segmentation model to segment the lung region image from the target image, wherein, the segmentation model corresponds to a lung segmentation model.

11. The method of claim 1, wherein the segmentation model used in connection with segmenting the target region image is selected based at least in part on an organ comprised in the target image.

12. The method of claim 1, wherein a classification of the disease or abnormality is based at least in part on one or more of: patient characteristics, a color of at least part of the organ comprised in the target object region, a size of the organ, a color variation across the organ, and an organ type corresponding to the organ.

13. The method of claim 1, further comprising:
    determining one or more proposed therapeutic regimens based at least in part on (i) a patient characteristic, and (ii) one or more of the lesion comprised in the target object region and the classified disease or abnormality; and
    providing the one or more proposed therapeutic regimens to a user via a user interface.

14. A medical imaging analysis system, comprising:
    medical imaging equipment configured to scan a patient and generate a first medical image of the patient;
    a front-end processor configured to:
    perform data masking with respect to the first medical image to obtain a second medical image;
    perform data filtering with respect to the second medical image to obtain a target image; and
    communicate an image to be recognized to an analysis terminal; and
    the analysis terminal configured to:
    obtain the target image;
    determine a target image source;
    select a target classification process based at least in part on the target image source, the target classification process comprising:
    segmenting a target region image from the target image wherein:
    the target region image is segmented from the target image based at least in part on a use of a segmentation model;
    the segmentation model is trained using a machine learning process; and
    the target region image comprises a target object region in the target image, the target object region being identified using the segmentation model;
    analyzing the target region image based at least in part on an organ lesion segmentation model to identify a lesion comprised in the target object region, wherein the organ lesion segmentation model is selected based at least in part on an organ comprised in the target object region, and the organ lesion segmentation model is a machine learning model; and
    analyzing, by the one or more processors, the target region image based at least in part on a disease recognition model to determine whether a patient associated with the target image has a disease or other abnormality, and classify any disease or abnormality afflicting the patient; and
    provide an image of the lesion and an indication of whether the patient has a particular disease or abnormality.

15. The analysis system of claim 14, wherein the analysis terminal is further configured to synchronously communicate the recognition result to an image filing and communication system or to communicate the recognition result to a client terminal and cause the client terminal to display a prompt message.

16. A device, comprising:
    one or more processors configured to:
    obtain a target image;
    determine a target image source;
    select a target classification process based at least in part on the target image source, the target classification process comprising:
    segmenting a target region image from the target image, wherein:
    the target region image is segmented from the target image based at least in part on a use of a segmentation model;

the segmentation model is trained using a machine learning process; and the target region image comprises a target object region in the target image, the target object region being identified using the segmentation model;

analyzing the target region image based at least in part on an organ lesion segmentation model to identify a lesion comprised in the target object region, wherein the organ lesion segmentation model is selected based at least in part on an organ comprised in the target object region, and the organ lesion segmentation model is a machine learning model; and analyzing, by the one or more processors, the target region image based at least in part on a disease recognition model to determine whether a patient associated with the target image has a disease or other abnormality, and classify any disease or abnormality afflicting the patient; and provide an image of the lesion and an indication of whether the patient has a particular disease or abnormality; and one or more memories coupled to the one or more processors, configured to provide the one or more processors with instructions.

17. A method, comprising:

obtaining, by one or more processors, a target image from a target image source, the target image being obtained based at least in part on one or more inputs corresponding to a user selection;

receiving, by the one or more processors, a user selection pertaining to an image analysis process;

determining, by the one or more processors, a target image analysis process based at least in part on the user selection of the image analysis process;

analyzing, by the one or more processors, the target image based at least in part on an organ lesion segmentation model to identify a lesion comprised in a target object region in the target image, wherein the organ lesion segmentation model is selected based at least in part on an organ comprised in the target object region, and the organ lesion segmentation model is a machine learning model;

analyzing, by the one or more processors, a target object region comprised in the target image based at least in part on a disease recognition model to determine whether a patient associated with the target image has a disease or other abnormality, and classify any disease or abnormality afflicting the patient, wherein the organ lesion segmentation model is selected based at least in part on an organ comprised in the target object region; and providing an image of the lesion and an indication of whether the patient has a particular disease or abnormality.

18. The method of claim 17, wherein determining the target image analysis process based at least in part on the user selection comprises:

obtaining at least one image analysis process corresponding to the target image source;

presenting said at least one image analysis process;

receiving a selection signal input by the user; and determining the target image analysis process from among the at least one image analysis process based at least in part on the selection signal.

19. A computer program product, the computer program product being embodied in a non-transitory computer readable storage medium and comprising computer instructions for:

obtaining, by one or more processors, a target image;

determining a target image source;

selecting a target classification process based at least in part on the target image source, the target classification process comprising:

segmenting, by the one or more processors, a target region image from the target image, wherein:

the target region image is segmented from the target image based at least in part on a use of a segmentation model;

the segmentation model is trained using a machine learning process; and the target region image comprises a target object region in the target image, the target object region being identified using the segmentation model;

analyzing, by the one or more processors, the target region image based at least in part on an organ lesion segmentation model to identify a lesion comprised in the target object region, wherein the organ lesion segmentation model is selected based at least in part on an organ comprised in the target object region, and the organ lesion segmentation model is a machine learning model; and analyzing, by the one or more processors, the target region image based at least in part on a disease recognition model to determine whether a patient associated with the target image has a disease or other abnormality, and classify any disease or abnormality afflicting the patient, wherein the organ lesion segmentation model is selected based at least in part on an organ comprised in the target object region; and providing an image of the lesion and an indication of whether the patient has a particular disease or abnormality.

20. A computer program product, the computer program product being embodied in a non-transitory computer readable storage medium and comprising computer instructions for:

obtaining, by one or more processors, a target image from a target image source, the target image being obtained based at least in part on one or more inputs corresponding to a user selection;

receiving, by the one or more processors, a user selection pertaining to an image analysis process;

determining, by the one or more processors, a target image analysis process based at least in part on the user selection image analysis process;

analyzing, by the one or more processors, the target image based at least in part on an organ lesion segmentation model to identify a lesion comprised in a target object region in the target image, wherein the organ lesion segmentation model is selected based at least in part on an organ comprised in the target object region, and the organ lesion segmentation model is a machine learning model;

analyzing, by the one or more processors, the object region comprised in the target image based at least in part on a disease recognition model to determine whether a patient associated with the target image has a disease or other abnormality, and classify any disease or abnormality afflicting the patient, wherein the organ lesion segmentation model is selected based at least in part on an organ comprised in the target object region; and providing an image of the lesion and an indication of whether the patient has a particular disease or abnormality.

* * * * *